US008050748B2

(12) United States Patent
Ali et al.

(10) Patent No.: US 8,050,748 B2
(45) Date of Patent: Nov. 1, 2011

(54) DECISION SUPPORT SYSTEM TO DETECT THE PRESENCE OF ARTIFACTS IN PATIENTS MONITORING SIGNALS USING MORPHOGRAMS

(75) Inventors: Walid Ali, Croton-on-Hudson, NY (US); Christopher S. Hall, Hopewell Junction, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 1479 days.

(21) Appl. No.: 10/597,081

(22) PCT Filed: Jan. 12, 2005

(86) PCT No.: PCT/IB2005/050136
§ 371 (c)(1),
(2), (4) Date: Jul. 11, 2006

(87) PCT Pub. No.: WO2005/071600
PCT Pub. Date: Aug. 4, 2005

(65) Prior Publication Data
US 2007/0185408 A1    Aug. 9, 2007

Related U.S. Application Data

(60) Provisional application No. 60/536,764, filed on Jan. 15, 2004.

(51) Int. Cl.
*A61B 5/04* (2006.01)
(52) U.S. Cl. ...................................................... 600/509
(58) Field of Classification Search ................... 600/509
See application file for complete search history.

(56) References Cited

U.S. PATENT DOCUMENTS

| 4,422,458 | A | * | 12/1983 | Kravath | ........................ 600/484 |
| 5,010,890 | A | | 4/1991 | Pfohl et al. | |
| 5,645,069 | A | | 7/1997 | Lee | |
| 6,304,775 | B1 | | 10/2001 | Iasemidis et al. | |
| 6,438,409 | B1 | | 8/2002 | Malik et al. | |
| 6,633,773 | B1 | * | 10/2003 | Reisfeld | ........................ 600/407 |
| 6,975,900 | B2 | * | 12/2005 | Rudy et al. | ..................... 600/523 |
| 2001/0025139 | A1 | | 9/2001 | Pearlman | |
| 2002/0082510 | A1 | | 6/2002 | Toole | |

FOREIGN PATENT DOCUMENTS

WO    WO 03/003905 A2    1/2003

OTHER PUBLICATIONS

Ali, W., et al.; Morphograms: Exploiting Correlation Patterns to Efficiently Identify Clinically Significant Events in Intensive Care Units; 2004; IEEE Proc. of EMBS; pp. 554-557.
Fojt, O., et al.; Applying Nonlinear Dynamics to ECG Signal Processing; 1998; IEEE Engineering in Medicine and Biology; pp. 96-101.
Kudo, M., et al.; Approximation of class regions by quasi convex hulls; 1998; Pattern Recognition Letters; 19:777-786.
Le Van Quyen, M., et al.; Nonlinear interdependencies of EEG signals in human intracranially recorded temporal lobe seizures; 1998; Brain Research; 792:24-40.

* cited by examiner

*Primary Examiner* — Michael Kahelin (57) ABSTRACT

A method for monitoring a patient (110) includes determining (114) convex hulls for pairs of monitored signals from the patient, and determining whether a perturbation has occurred (115, 116) in one or more of the convex hulls. This exemplary embodiment (110) can also include alerting an operator that a clinically significant change may have occurred (117) in the patient if each of the convex hulls has been perturbed. If only a subset of the convex hulls is perturbed, an artifact has probably occurred (118).

20 Claims, 7 Drawing Sheets

DECISION SUPPORT SYSTEM TO DETECT THE PRESENCE OF ARTIFACTS IN PATIENTS MONITORING SIGNALS USING MORPHOGRAMS

CROSS REFERENCE TO RELATED APPLICATIONS

This application claims the benefit of U.S. provisional application Ser. No. 60/536,764 filed Jan. 15, 2004, which is incorporated herein by reference.

DESCRIPTION

The present invention relates generally to expert systems, and more particularly to an expert system for use in assisting a providing healthcare to a patient.

Healthcare technology (e.g., biomedical sensors, monitoring systems and medical devices) is rapidly advancing in capability as well as sheer prevalence (numbers of devices) in the modern intensive care unit (ICU). The creation of additional data streams is imposing a significant "information-overload" challenge upon healthcare staff that also faces a critical shortage of intensive care staff to meet the needs of the ICU patient population.

The present invention is therefore directed to the problem of developing a method and apparatus for reducing the amount of information that must be processed manually in an intensive care environment or other healthcare environment.

The present invention solves this and other problems by providing a method and apparatus composed of intelligent modules, which are capable of assimilating multiple data streams originating from a broad array of sensors and systems and able to distinguish clinically-significant changes in patient states from clinically-insignificant changes or artifacts.

According to one aspect of the present invention, a method for monitoring a patient includes: determining a first convex hull for a first set of points, each point of the first set of points having a first coordinate being a value of a first monitored signal at a specific moment in time, and having a second coordinate being a value of a second monitored signal at the specific moment in time, and determining a second convex hull for a second set of points, each point of the second set of points having a first coordinate being a value of a third monitored signal at a specific moment in time, and having a second coordinate being a value of a fourth monitored signal at the specific moment in time. The method also includes monitoring the first and second convex hulls to determine whether a perturbation has occurred in either of the first and second convex hulls, determining, upon detecting a perturbation in one of the first and second convex hulls, whether a perturbation has occurred in the other of the first and second convex hulls, and alerting an operator that a clinically significant change may have occurred in the patient if both the first and second convex hulls have been perturbed.

According to another aspect of the present invention, a method for monitoring a patient includes determining convex hulls for pairs of monitored signals from the patient, and determining whether a perturbation has occurred in one or more of the convex hulls. This exemplary embodiment can also include alerting an operator that a clinically significant change may have occurred in the patient if each of the convex hulls has been perturbed.

According to yet another aspect of the present invention, a method for monitoring a patient includes determining convex hulls for pairs of monitored signals from the patient, and indicating a potentially clinically significant change based on a determination that a perturbation has occurred in each of the convex hulls. This embodiment of a method for monitoring a patient can also include determining that a perturbation has occurred in one of the convex hulls, evaluating one or more remaining ones of the convex hulls to determine whether a perturbation has occurred in each of the one or more remaining ones of the convex hulls, upon determining that a perturbation has occurred in the one or more remaining ones of the convex hulls, determining that a clinically significant change may have occurred in the patient, and upon determining that a perturbation has not occurred in the one or more remaining ones of the convex hulls, determining that an artifact may exist in the pairs of monitored signals.

According to still another aspect of the present invention, a method for monitoring a patient includes indicating that a clinically significant change may have occurred in the patient if perturbations exist in convex hulls of plots of monitored signal pairs; and indicating that an artifact may exist in one or more monitored signals if a perturbation exists only in a subset of the convex hulls of the plots of monitored signal pairs and not in a remaining ones of the convex hulls of the plots of monitored signal pairs.

According to yet another aspect of the present invention, an apparatus for monitoring a patient includes a processor and a memory. Multiple leads, each receiving a monitored signal from the patient, connect the processor to the patient. The memory stores a value of each of the leads at a multiple points in time. The processor determines convex hulls for multiple pairs of signals from the leads, and determines whether a perturbation has occurred in one or more of the convex hulls. This embodiment can also include a interface coupled to the memory and the processor, wherein the processor outputs an alert signal to the user interface to indicate that a clinically significant change may have occurred in the patient if perturbations exist in a plurality of convex hulls of a plurality of plots of monitored signal pairs, or indicating that an artifact may exist in one or more of a plurality of monitored signals if a perturbation exists only in a subset of the plurality of convex hulls of the plurality of plots of monitored signal pairs and not in a remaining ones of the plurality of convex hulls of the plurality of plots of monitored signal pairs. This embodiment can also include a display coupled to the processor to display each of the signals from the leads and to display plots of each of the signals with respect to one another. In some cases, the display can overlay a calculated convex hull for each of the plots.

The above methods can also be stored in computer readable media as instructions for programming a processor to monitor a patient.

It is worthy to note that any reference herein to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

As used herein, a monitored signal comprises any signal that is being monitored by a monitoring device or system. Examples of monitored signals include but are not limited to electrocardiogram signals, morphogram signals, pulse rate signals, respiratory signals, brain waves, etc.

The present invention includes a system composed of intelligent modules, which are capable of assimilating multiple data streams originating from a broad array of sensors and systems and able to distinguish clinically-significant changes in patient states versus clinically-insignificant changes or artifacts. The present invention includes a method for data stream fusion, which will enable multi-parameter monitoring capabilities.

The present invention also includes a method and a system to detect artifacts in a given monitored signal (or a set of monitored signals) based on the collective behavior of the set of monitored signals (e.g., morphograms), which represents the patient's current clinical conditions.

Morphograms represent the relationship between two signals by showing the loci of the time variation. Morphograms are already used in MRI for gating, where images have to be captured at an exact point of time. It's used for the diagnosis of coronary artery disease using MRI and for hemodynamic illustration.

Figure 1:
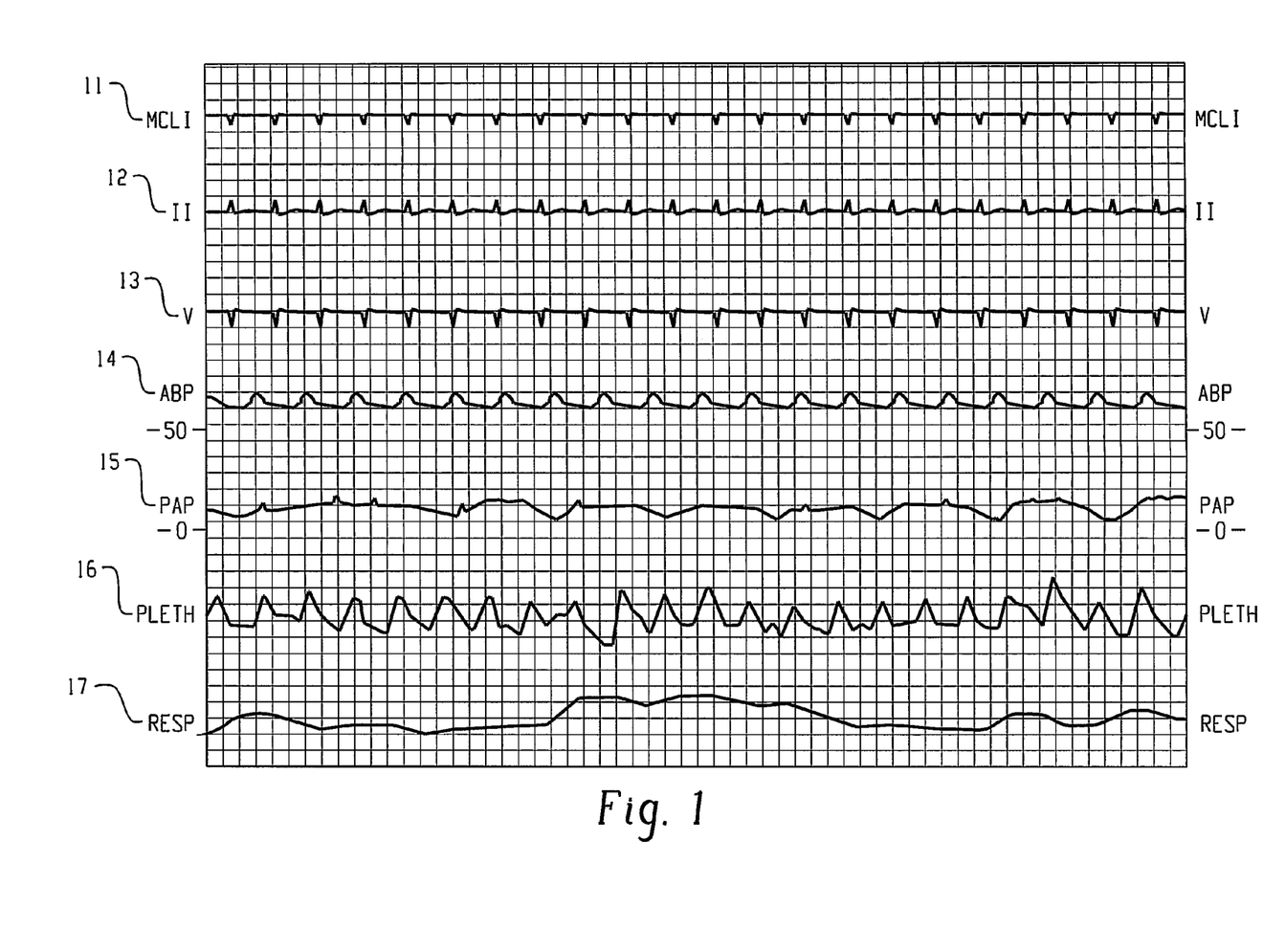
FIG. 1 depicts an exemplary embodiment of a flow chart of a method for processing multiple data streams according to one aspect of the present invention.

The physician (or expert) validates the correctness of the hemodynamic signals recorded for a short span of time (generally, monitoring systems record ~125 sample per second, so, a few minutes period is adequate). FIG. 1 shows a sample of such signals that are accepted as valid signals for the patient under examination. For example, FIG. 1 shows the MCL1 11, II 12, V 13, ABP 14, PAP 15, PLETH 16 and RESP 17 lead signals from a morphogram system. These represent examples of monitored signals.

Plotting the relationship between every pair of signals under study (for this case, let's look at the II 12, V 13 and the ABP 14 signals) gives loci of the relationship between every pair as it changes with time.

Figure 2:
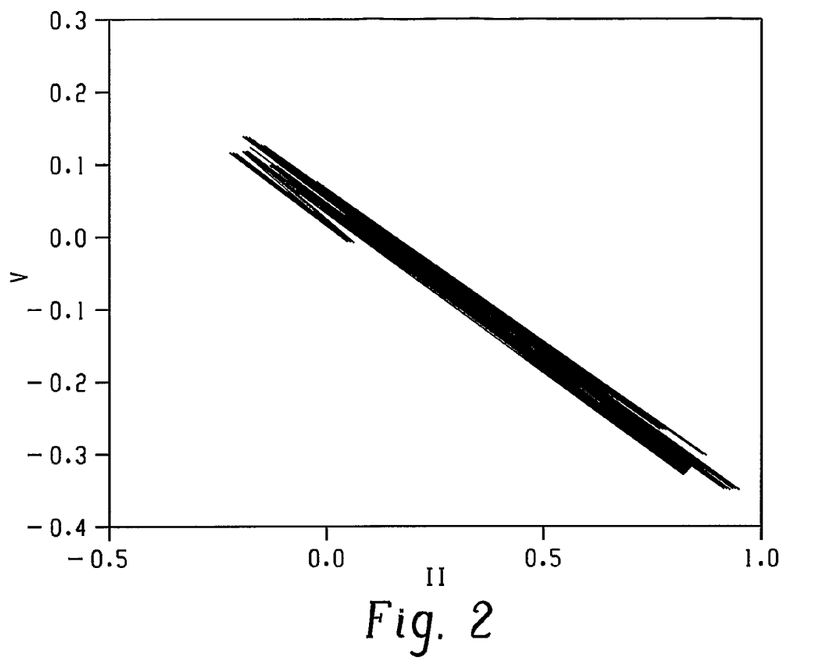
FIGS. 2-4 depict vector cardiograms of II 12, V 13 and ABP 14 signals for a Respiratory Failure Patient.
Figure 3:
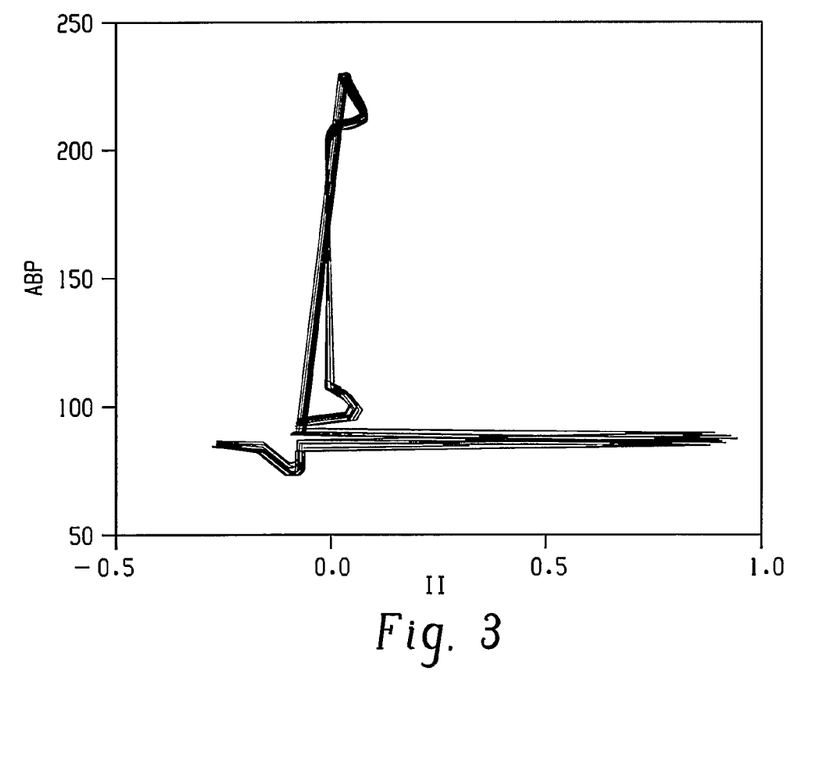
Figure 4:
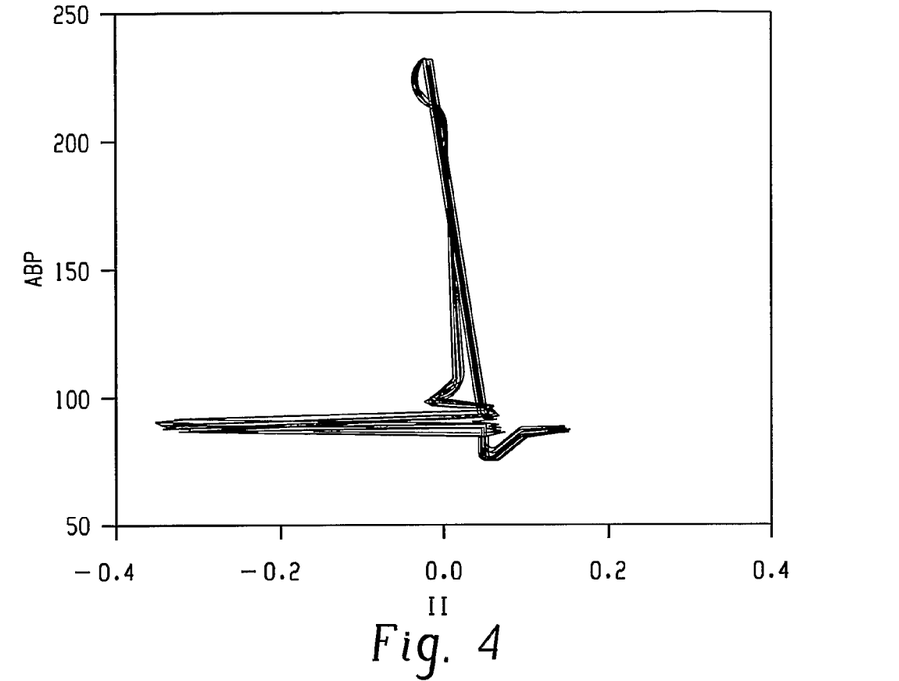

FIGS. 2-4 shows a plot of the relationship between pairs of signals for the II 12 and V 13 leads, as well as the ABP 14, respectively, on a patient with respiratory failure. With three signals of interest, one can plot three simultaneous plots (as shown in FIGS. 2-4) to capture the hemodynamic changes in the patient with time.

Figure 5:
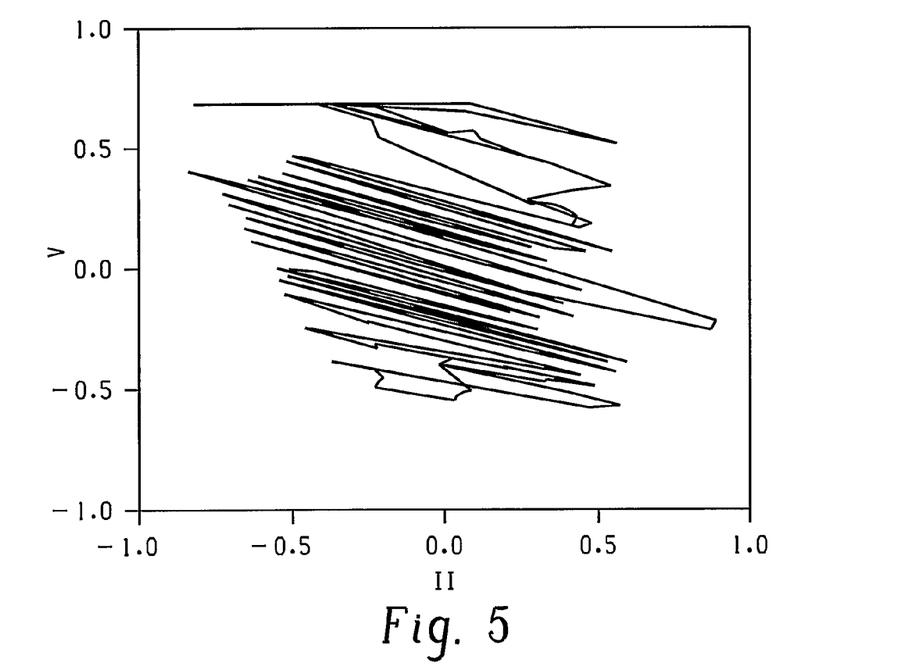
FIGS. 5-7 depict an example of proportional perturbations in all the morphograms for a respiratory failure patient due to a potentially clinically significant change in the patient according to one aspect of the present invention.
Figure 6:
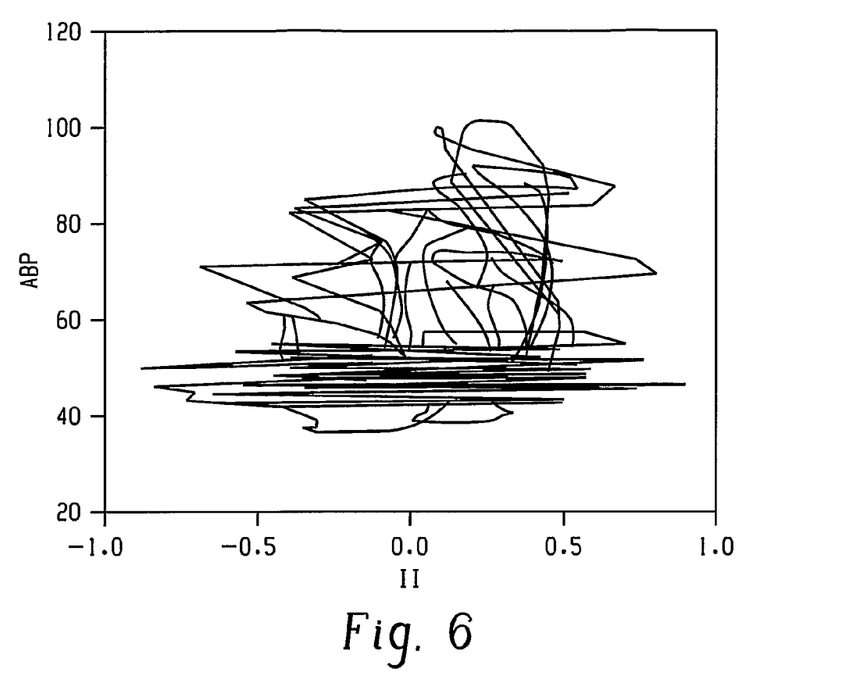
Figure 7:
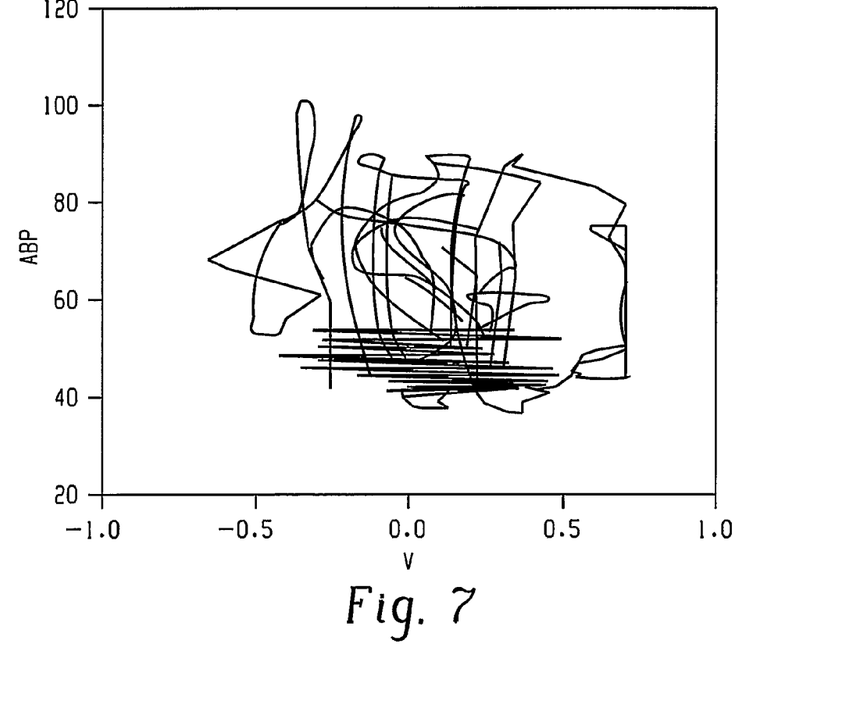

Each of the subplots has a well-defined shape that repeats itself with time as long as the patient is not undergoing any clinically significant changes. As there is a persistent pattern of correlation between the hemodynamic measures, an isolated change (e.g., a change in a single subplots/morphogram) that is not accompanied by comparable changes in the remaining morphogram subplots reflects a substantial problem with the signals being plotted in this subplot, such as the presence of an artifact. However, a comparable change (or perturbation) in ALL the signals' morphograms comprises a clear indication of a clinically significant change in the patient's condition and is NOT due to artifacts. FIGS. 5-7 show the perturbations with the same patient due to clinical changes in the patient's condition for the same II 12, V 13 and ABP 14 signals plotted with respect to each other.

According to one aspect of the present invention, perturbations due to clinical changes in the patient's condition can be distinguished from perturbations due to artifacts, in that the perturbation due to an artifact will only take place in a number of the morphogram subplots and not all of the subplots, whereas perturbations due to a change in a patient's clinical condition will occur in all of the morphogram subplots. For example, a movement by the patient that affects lead II 12 but not others will affect the plots in which the relationship between the signal from lead II and other signals is being plotted. Thus, more than one plot can be affected by an artifact in a single lead signal, but not all.

Figure 8:
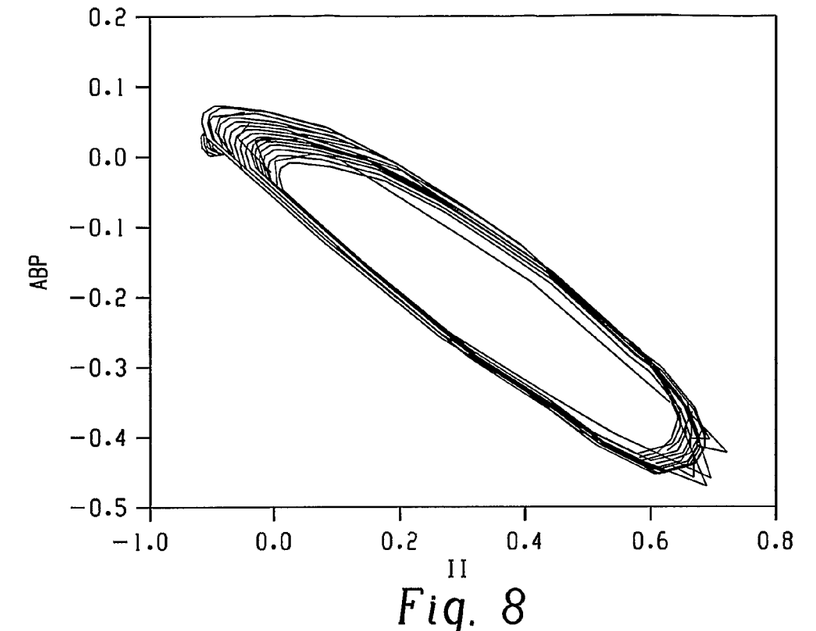
FIGS. 8-10 depict an example of non-consistent perturbations in the different morphograms that indicates artifacts presence according to another aspect of the present invention.
Figure 9:
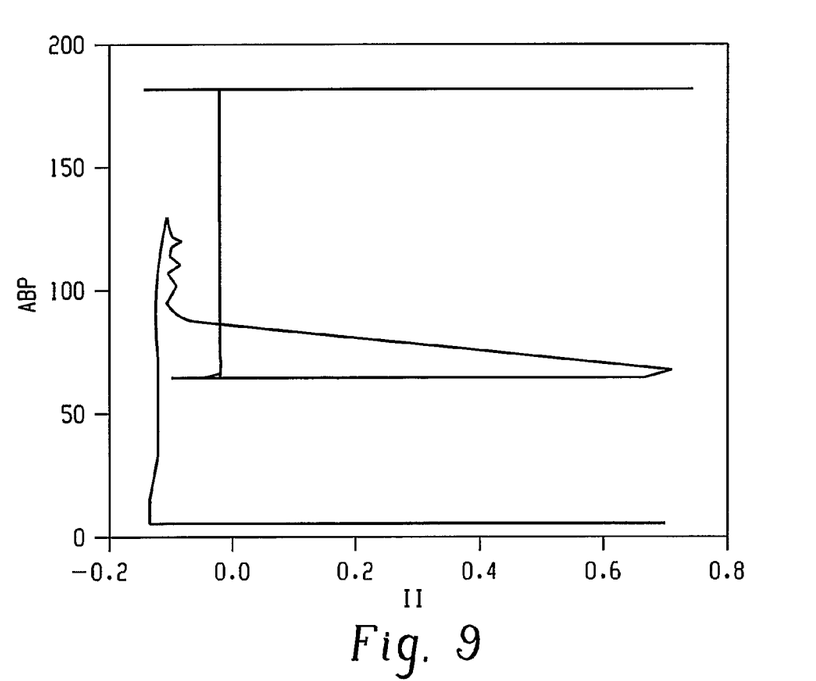
Figure 10:
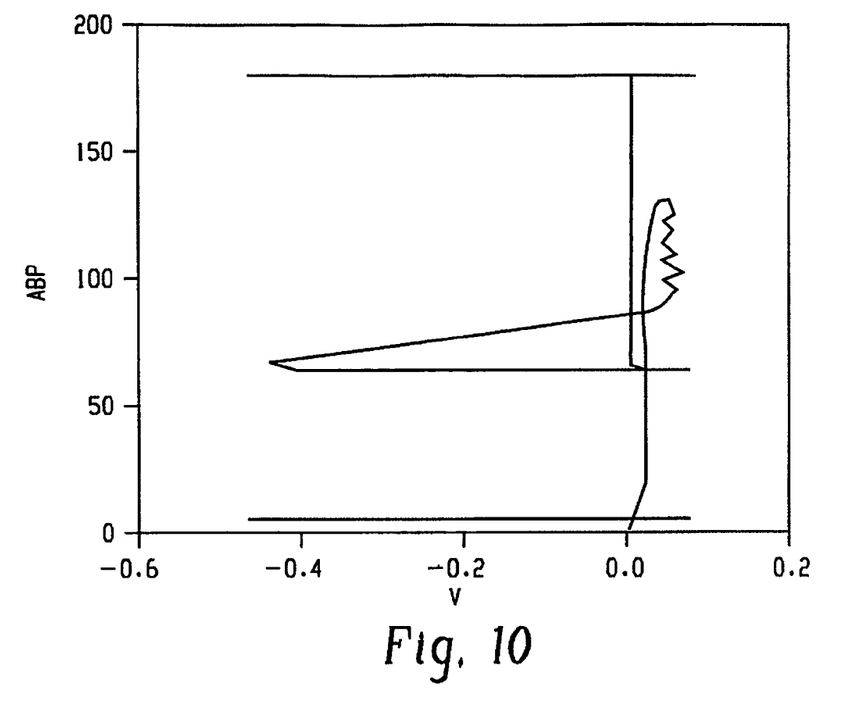

FIGS. 8-10 shows the result of an artifact present in signals being monitored from a patient on the various subplots used in FIGS. 2-7 in a patient with pulmonary edema. The shape perturbations apparent in FIGS. 9 and 10 (i.e., the second and third morphogram subplots) are not proportional to the perturbation on the first morphogram subplot (which is the only ECG-based morphogram). This is a clear indication of artifact presence in the signal common in the second and third morphogram subplots, namely, the ABP 14 signal.

According to another aspect of the present invention, the shape perturbation can be easily and efficiently quantified by examining the convex hull of the shape under study. A convex hull is the smallest convex set containing the points at issue. One can think of a convex hull as a rubber band wrapped around the "outside" points. Convex hulls are unique and can be efficiently computed for a random number of points.

According to another aspect of the present invention, a method for detecting artifacts can be summarized as:

Is shape (Convex hull) perturbed in a SUBSET of morphogram subplots?

Figure 11:
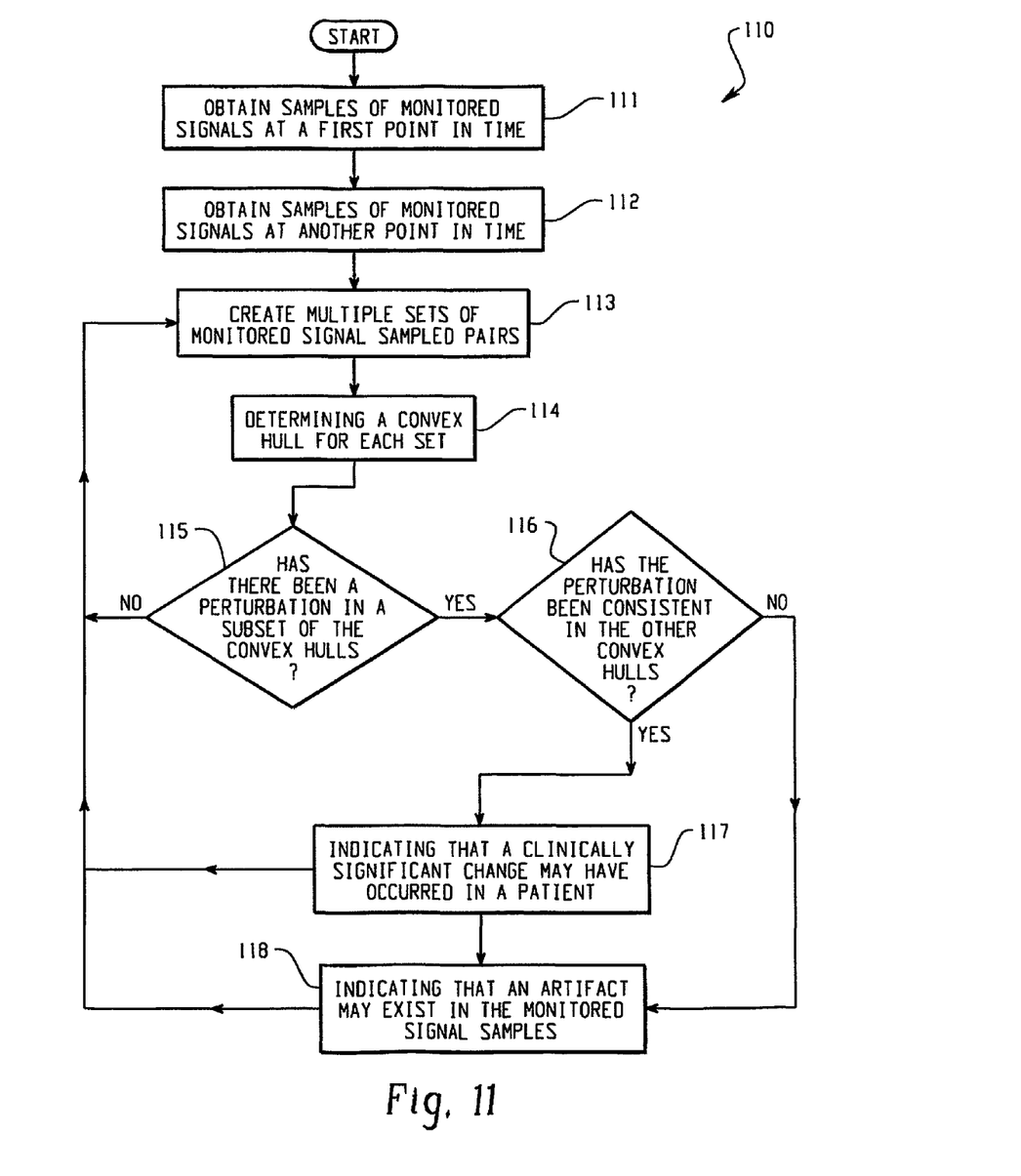
FIG. 11 depicts an exemplary embodiment of a method for monitoring a patient according to yet another aspect of the present invention.

If yes:
Is shape (Convex hull) perturbed consistently in the remaining?
If yes→No artifacts but CLINICALLY SIGNIFICANT
Else ARTIFACT detected in the monitored signal Turning to FIG. 11, shown therein is an exemplary embodiment 110 of a method for monitoring a patient.

In step 111, electrocardiogram samples are obtained from a patient at a first moment in time. For example, samples E11, E21, E31 are obtained from electrode 1, electrode 2 and electrode 3 at time t1.

In step 112, electrocardiogram samples are obtained from a patient at another moment in time. For example, samples E12, E22, E32 are obtained from electrode 1, electrode 2 and electrode 3 at time t2.

In step 113, multiple sets of electrode sample pairs are created. For example, set S12={P121, P122, ..., P12n} is created from a pair of samples, in which P121=(E11, E21), P122=(E12, E22), and P12n=(E1n, E2n). Set S13={P131, P132, ..., P13n} is created, in which P131=(E11, E31), P132=(E12, E32), and P13n=(E1n, E3n). Set S23={P231, P232, ..., P23n} is created, in which P231=(E21, E31), P232=(E22, E32), and P23n=(E2n, E3n). For more than three samples, similar sets would be created for the other pairs.

In step 114, convex hulls are created for each set of points. Any standard technique can be employed for calculating the convex hull. For example, one technique known as the Gift Wrapping algorithm operates as follows:

(1) Find least point A (with minimum y coordinate) as a starting point.

(2) Find B where all points lie to the left of AB by scanning through all the points. To determine if a point is to the left of the line AB can be determined by calculating the area of a triangle involving the three points of interest (i.e., the two on line AB and the point of interest). The area of the triangle P0P1P2 where P0=(x0,y0), P1=(x1,y1) and P2=(x2,y2) is:

$$\frac{1}{2}\begin{vmatrix} x0 & x1 & x2 \\ y0 & y1 & y2 \\ 1 & 1 & 1 \end{vmatrix}$$

If the area is positive then the points occur in anti-clockwise order and P2 is to the left of the line P0P1. If the convex hull is kept in anti-clockwise order then this area will be positive for any three consecutive points on the hull. If the area is negative then they are in clockwise order. Finally, if the area is zero the three points are collinear.

(3) Find C where all points lie to the left of BC.

(4) Repeat step 3 to find the next point and so on until reaching point A.

Other algorithms may be used to determine the convex hulls.

In step 115, each of the convex hulls are monitored to determine whether there are any perturbations in them. A perturbation can be determined by comparing the current convex hull to the prior convex hull and identifying a significant difference, such as a new vertex that lies a significant difference away from a last vertex. For example, a significant difference could be a value that lies several standard deviations from the mean, or some large percentage difference from the centroid or other predetermined threshold.

In step 116, once a perturbation is noted in one of the convex hulls, each of the other convex hulls is examined for similar perturbations.

In step 117, a clinically significant change is identified as potentially having occurred as similar perturbations are detected in each of the convex hulls.

In step 118, an artifact is determined to possibly exist in the electrocardiogram signals as no similar or consistent perturbations have been detected in the other convex hulls, despite there being perturbations in a subset of convex hulls.

The process then continues as long as the patient is being monitored. In each of the determinations in steps 117-118, a user can be notified so that a physician, if necessary or desired, can make a medical judgment.

Figure 12:
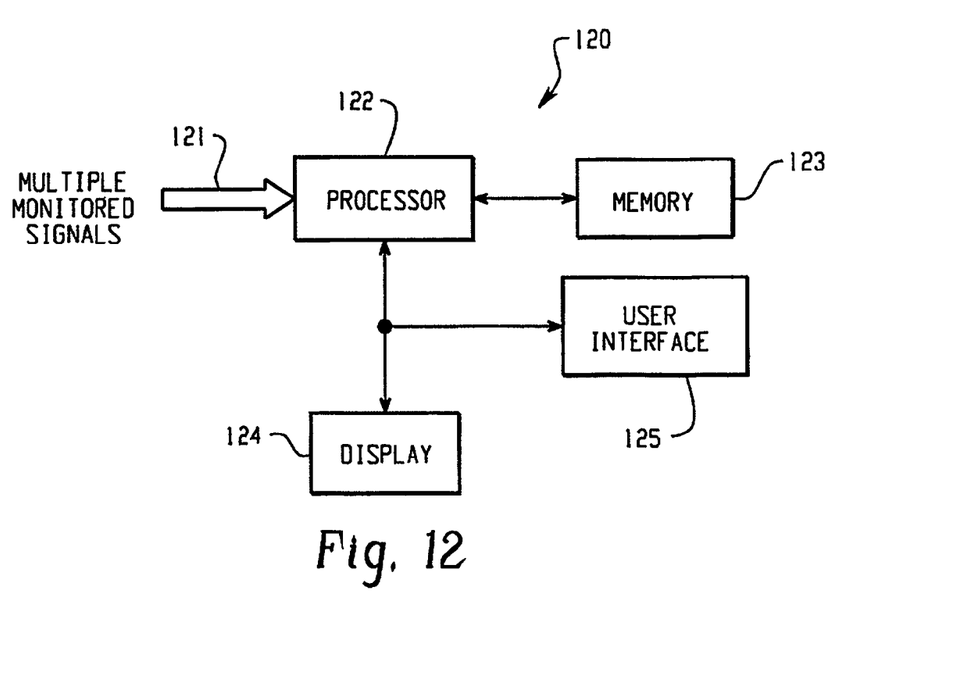
FIG. 12 depicts an exemplary embodiment of an apparatus for monitoring a patient according to still another aspect of the present invention.

Turning to FIG. 12, shown therein is an exemplary embodiment of an apparatus for monitoring a patient according to yet another aspect of the present invention. The apparatus 120 includes multiple leads 121 to connect to a patient or other monitoring equipment to obtain the monitored signals.

The monitored signals are then fed to a processor 122 that determines the various interrelationships between the various monitored signals, as described above. The processor also calculates the convex hull for each of the interrelationships determined. The plot of the interrelationships and the convex hulls can be displayed on display 124. Any processor capable of performing these relatively simple calculations can be employed, such as an Intel Pentium processor, or a computer having this chip as its main cpu.

All programming necessary to program processor 122 can be stored in memory 123. Memory 123 can also store the values being used by the processor to determine whether clinically significant events have occurred or whether an artifact has created noise in the monitored signal or signals. Memory 123 can also store intermediate calculations necessary by processor 122 to arrive at the above-described determinations. Memory 123 can be a random access memory having a capacity sufficient to store several days worth of samples of the monitored signals, as well as the programming necessary to program processor 122 and memory used by processor 122 to support its calculations. Several gigabytes should be sufficient for this purpose. Memory 122 can also be a disk drive, a series of memory sticks, etc.

User interface includes a keyboard, a mouse and other audio and visual indicators that alert an operator that a clinically significant change may have occurred in a patient, as opposed to an artifact, which may also require attention.

Although various embodiments are specifically illustrated and described herein, it will be appreciated that modifications and variations of the invention are covered by the above teachings and are within the purview of the appended claims without departing from the spirit and intended scope of the invention. For example, certain signals are discussed as being monitored signals, however, other signals are also possible for use in the techniques herein without departing from the scope of the present invention. Moreover, certain techniques for calculating the convex hull are set forth herein, but other techniques would also suffice. Furthermore, these examples should not be interpreted to limit the modifications and variations of the invention covered by the claims but are merely illustrative of possible variations.

The invention claimed is:

1. An apparatus for monitoring a patient comprising:
 a plurality of leads carrying monitored signals from the patient;
 a memory which stores values of the monitored signals carried on each of the plurality of leads at a plurality of points in time;
 a processor coupled to each of the plurality of leads, said processor being programmed to:
  calculate convex hulls for each of a plurality of pairs of monitored signals from the plurality of leads,
  determine when a perturbation has occurred in one or more of the plurality of convex hulls,
  in response to determining that a perturbation has occurred in one or more of the convex hulls, generating an alert signal; and
 a user interface coupled with the processor to receive the alert signal and present a corresponding alert to a user.

2. The apparatus according to claim 1, wherein said processor outputs the alert signal to the user interface to indicate that a clinically significant change may have occurred in the patient when perturbations exist in a plurality of convex hulls of a plurality of plots of monitored signal pairs, or indicating that an artifact may exist in one or more of a plurality of monitored signals when a perturbation exists only in a subset of the plurality of convex hulls of the plurality of plots of monitored signal pairs and not in a remaining plurality of convex hulls of the plurality of plots of monitored signal pairs.

3. The apparatus according to claim 1, wherein the user interface includes a display coupled to the processor to display each of the plurality of signals from the plurality of leads and to display a plurality of plots of each of the plurality of signals with respect to one of the other plurality of signals.

4. The apparatus according to claim 3, wherein said display overlays a calculated convex hull for each of the plurality of plots.

5. The apparatus according to claim 1, wherein the processor is further programmed to:
 determine whether a perturbation has occurred in all of the convex hulls, in response to a perturbation having occurred in all of the convex hulls, the generated alert signal indicating that a clinically significant change in the patient has occurred.

6. The apparatus according to claim 5, wherein the processor is further programmed to:
   determine whether a perturbation has occurred in only some of the complex hulls but not all of the complex hulls, in response to determining that a perturbation has occurred in only some of the convex hulls, the generated alert signal indicating that an artifact may exist.

7. The apparatus according to claim 1, wherein the processor is further programmed to:
   determine whether a perturbation has occurred in only some of the complex hulls but not all of the complex hulls, in response to determining that a perturbation has occurred in only some of the convex hulls, the generated alert signal indicating that an artifact may exist.

8. The apparatus according to claim 1, wherein the processor is further programmed to:
   generate plots of the monitored signals;
   overlay the calculated convex hull with each of the plots; and
   control the user interface to display the overlayed plots and convex hulls.

9. The apparatus according to claim 1, wherein the processor is further programmed to:
   quantify a shape of the perturbations of the convex hulls.

10. The apparatus according to claim 1, wherein the processor is further programmed to:
    determine whether perturbations in a plurality of the convex hulls are proportional.

11. The apparatus according to claim 1, wherein determining whether the perturbation has occurred includes:
    comparing a current convex hull with a prior convex hull to determine a difference.

12. The apparatus according to claim 11, wherein determining the perturbation further includes at least one of:
    determining whether a vertex of the current convex hull is different from a vertex of the previous convex hull; and
    determining whether a centroid of a current convex hull is different from a centroid of the previous convex hull.

13. An apparatus for monitoring a patient comprising:
    a plurality of leads carrying first, second, third, and fourth monitored signals from a patient;
    a memory which stores values of the first, second, third, and fourth monitored signals at a plurality of points in time;
    a processor coupled to the leads and the memory, the processor being programmed to:
      determine a first convex hull for a first plurality of points, each point of the first plurality of points having a first coordinate being a value of the first monitored signal at a specific moment in time, and having a second coordinate being a value of the second monitored signal at the specific moment in time,
      determine a second convex hull for a second plurality of points, each point of the second plurality of points having a first coordinate being a value of the third monitored signal at the specific moment in time, and having a second coordinate being a value of the fourth monitored signal at the specific moment in time,
      monitoring the first and second convex hulls to determine when a perturbation has occurred in either of the first and second convex hulls,
      determining, upon detecting a perturbation in one of the first and second convex hulls, whether a perturbation has occurred in the other of the first and second convex hulls; and
    a user interface connected with the processor by which in response to the processor determining that an operator is alerted that a clinically significant change may have occurred in the patient if both the first and second convex hulls have been perturbed.

14. The method for monitoring a patient comprising:
    carrying a plurality of monitored signals on a plurality of leads;
    in a memory, storing values of the monitored signals carried on each of the plurality of leads at a plurality of points in time;
    with a processor coupled to each of the plurality of leads performing the steps of:
      calculating convex hulls for each of a plurality of pairs of the monitored signals from the plurality of leads,
      determining when a perturbation has occurred in one or more of the convex hulls,
      in response to determining that a perturbation has occurred in one or more of the convex hulls, generating an alert signal; and
    with a user interface, receiving the alert signal from the processor and presenting a corresponding alert to a user.

15. The method according to claim 14, further including:
    determining whether a perturbation has occurred in all of the convex hulls, in response to a perturbation having occurred in all of the convex hulls, the generated alert signal indicates that a clinically significant change in the patient has occurred.

16. The method according to claim 14, further including:
    determining whether a perturbation has occurred in only some of the convex hulls, but not in all of the convex hulls, in response to determining that a perturbation has occurred in only some of the convex hulls, the generated alert signal indicates that an artifact may exist.

17. The method according to claim 14, further including at least one of:
    quantifying a shape of the perturbations of the convex hulls;
    determining whether determined perturbations in a plurality of the convex hulls are proportional.

18. The method according to claim 14, wherein determining whether a perturbation has occurred includes:
    comparing a current convex hull with a prior convex hull.

19. A method for monitoring a patient comprising:
    carrying first, second, third, and fourth monitored signals from a patient on a plurality of leads;
    storing values of the first, second, third, and fourth monitored signals at a plurality of points in time in a memory;
    with a processor:
      determining a first convex hull for a first plurality of points, each point of the first plurality of points having a first coordinate being a value of the first monitored signal at a specific moment in time, and having a second coordinate being a value of the second monitored signal at the specific moment in time,
      determining a second convex hull for a second plurality of points, each of the second plurality of points having a first coordinate being a value of the first monitored signal at a specific moment in time, and having a second coordinate being a value of the fourth monitored signal at the specific moment in time;
      determining, upon detection of a perturbation in one of the first and second convex hulls, whether a perturbation has occurred in the other of the first and second convex hulls;
    with a user interface, alerting an operator that a clinically significant change may have occurred in the patient in response to determining that both the first and second convex hulls have been perturbed.

20. A non-transitory computer readable medium carrying software which controls one or more processors to perform the steps of:
- receiving a plurality of monitored signals carried on a plurality of leads;
- storing values of the monitored signals carried on the plurality of leads at a plurality of points in time, in a memory;
- calculating convex hulls for each of a plurality of pairs of the monitored signals from the plurality of leads;
- determining when a perturbation has occurred in one or more of the convex hulls;
- in response to determining that a perturbation has occurred in one or more of the convex hulls, generating an alert signal; and
- controlling a user interface to receive the alert signal and to present a corresponding alert to a user.

* * * * *